(12) United States Patent
Bristow

(10) Patent No.: US 10,131,609 B2
(45) Date of Patent: Nov. 20, 2018

(54) PROCESS FOR THE CO-PRODUCTION OF ACETIC ACID AND DIMETHYL ETHER

(71) Applicant: BP CHEMICALS LIMITED, Middlesex (GB)

(72) Inventor: Timothy Crispin Bristow, East Yorkshire (GB)

(73) Assignee: BP CHEMICALS LIMITED, Middlesex (GB)

( * ) Notice: Subject to any disclaimer, the term of this patent is extended or adjusted under 35 U.S.C. 154(b) by 0 days.

(21) Appl. No.: 15/312,017

(22) PCT Filed: Jun. 12, 2015

(86) PCT No.: PCT/EP2015/063148
§ 371 (c)(1),
(2) Date: Nov. 17, 2016

(87) PCT Pub. No.: WO2015/193183
PCT Pub. Date: Dec. 23, 2015

(65) Prior Publication Data
US 2017/0107165 A1     Apr. 20, 2017

(30) Foreign Application Priority Data
Jun. 20, 2014   (EP) .................... 14173349

(51) Int. Cl.
*C07C 51/09*     (2006.01)
*C07C 67/37*     (2006.01)
*C07C 41/16*     (2006.01)

(52) U.S. Cl.
CPC .............. *C07C 51/09* (2013.01); *C07C 41/16* (2013.01); *C07C 67/37* (2013.01)

(58) Field of Classification Search
CPC .......... C07C 51/09; C07C 41/16; C07C 67/37
See application file for complete search history.

(56) References Cited

U.S. PATENT DOCUMENTS 4,802,956 A * 2/1989 Dornhagen .............. B01D 3/14
203/42
7,465,822 B2  12/2008 Cheung et al.

FOREIGN PATENT DOCUMENTS

| EP | 1 985 362 A1 | 10/2008 |
|---|---|---|
| WO | WO 2008/132438 A1 | 11/2008 |
| WO | WO 2008/132441 A1 | 11/2008 |
| WO | WO 2011/027105 A1 | 3/2011 |
| WO | WO 2013/124404 A1 | 8/2013 |
| WO | WO 2013/124423 A1 | 8/2013 |

* cited by examiner

*Primary Examiner* — Yate' K Cutliff
(74) *Attorney, Agent, or Firm* — McDonnell Boehnen Hulbert & Berghoff LLP

(57) ABSTRACT

Process for the co-production of acetic acid and dimethyl ether by dehydration-hydrolysis of a feed mixture of methanol and methyl acetate in the presence of at least one catalyst to generate a crude reaction product comprising acetic acid and dimethyl ether. The feed to the co-production process contains methanol and methyl acetate and also contains dimethyl ether in a total amount of 25 mol % or less based on the total feed.

18 Claims, 4 Drawing Sheets

PROCESS FOR THE CO-PRODUCTION OF ACETIC ACID AND DIMETHYL ETHER

This application is the U.S. national phase of International Application No. PCT/EP2015/063148 filed Jun. 12, 2015 which designated the U.S. and claims priority to European Patent Application No. 14173349.3 filed Jun. 20, 2014, the entire contents of each of which are hereby incorporated by reference.

The present invention relates to a process for the co-production of acetic acid and dimethyl ether, and in particular to a process for the co-production of acetic acid and dimethyl ether with improved conversion to products.

BACKGROUND OF THE INVENTION

Processes for the co-production of acetic acid and dimethyl ether may be carried out by the catalytic dehydration and hydrolysis of mixtures of methanol and methyl acetate. Such co-production processes are known from, for example WO 2011/027105, WO 2013/124404 and WO 2013/124423.

WO 2011/027105 describes a process for the production of acetic acid and dimethyl ether by contacting methanol and methyl acetate with a catalyst composition at a temperature in the range 140 to 250 C. wherein the catalyst composition contains a zeolite having a 2-dimensional channel system comprising at least one channel which has a 10-membered ring.

WO 2013/124404 describes a process for the co-production of acetic acid and dimethyl ether products from a mixture of methanol and methyl acetate by contacting the mixture at a temperature from 200 to 260 C. with a catalyst composition comprising a zeolite possessing a 2-dimensional channel system comprising at least one channel having a 10-membered ring and a silica:alumina molar ratio of at least 22:1.

WO2013/124423 describes a process for the production of acetic acid and dimethyl ether by contacting a mixture of methanol and methyl acetate with a zeolite catalyst wherein the zeolite has a 2-dimensional channel system comprising at least one channel having a 10-membered ring and having at least 5% of its cation exchange capacity occupied by one or more alkali metal cations.

Co-production processes to produce acetic acid and dimethyl ether from methyl acetate and methanol feed stocks can be represented by equations (1) and (2):

(1)

(2)

Sources of methyl acetate suitable for use in such co-production processes may be, for example methyl acetate-containing streams derived from processes for carbonylating dimethyl ether with carbon monoxide in the presence of a carbonylation catalyst to produce methyl acetate. Carbonylation processes of this type are known from, for example U.S. Pat. No. 7,465,822, WO 2008/132441 and WO 2008/132438. However, it has now been found that operation of such processes can result in crude product streams which are sub-optimal for direct utilisation in co-production processes of the type described above and in particular, those crude product streams which comprise significant amounts of dimethyl ether, such as crude product streams formed in carbonylation processes operated under low carbon monoxide partial pressure conditions.

Furthermore, direct utilisation of crude methyl acetate feed streams containing fairly high levels of dimethyl ether in co-production processes of the type described above has been found to inhibit the formation of dimethyl ether product and/or acetic acid product. This disadvantage may be further exacerbated by the use of commercial methanol sources which typically contain dimethyl ether and in amounts which may be in excess of 25 mol %.

SUMMARY OF THE INVENTION

Thus, there remains a need for an improved process for the co-production of acetic acid and dimethyl ether from methanol and methyl acetate streams which process has improved conversion to at least dimethyl ether product, and in particular an improved process for the co-production of acetic acid and dimethyl ether from methanol and methyl acetate streams derived from processes for the carbonylation of dimethyl ether with carbon monoxide in the presence of a carbonylation catalyst.

Accordingly, the present invention provides a process for the co-production of acetic acid and dimethyl ether by dehydration-hydrolysis of a feed mixture of methanol and methyl acetate in the presence of at least one catalyst to generate a crude reaction product comprising acetic acid and dimethyl ether wherein the feed to said co-production process comprising methanol and methyl acetate comprises dimethyl ether in a total amount of 25 mol % or less based on the total feed.

In preferred embodiments of the present invention, the feed for the co-production process has a total dimethyl ether content of 15 mol % or less, for example 10 mol % or less, preferably 5 mol % or less.

In one or more embodiments of the present invention the methyl acetate feed for the co-production process comprises methyl acetate and dimethyl ether. Suitably, the methyl acetate feed is derived from a crude methyl acetate stream produced in processes for the carbonylation of dimethyl ether with carbon monoxide in the presence of a carbonylation catalyst, for example a zeolite carbonylation catalyst and optionally hydrogen, to produce a crude methyl acetate stream comprising methyl acetate and dimethyl ether which crude methyl acetate stream is treated to reduce its dimethyl ether content to provide a methyl acetate feed to the co-production process which comprises dimethyl ether in an amount of >0 to 25 mol %, for example >0 to 15 mol %, such as >0 to 10 mol %, preferably >0 to 5 mol %.

In preferred embodiments of the present invention, a crude methyl acetate stream comprising methyl acetate and dimethyl ether is treated to reduce its dimethyl ether content by distillation, preferably by fractional distillation. Preferably, in these embodiments the crude methyl acetate stream is treated by fractional distillation in a distillation column wherein
  (i) dimethyl ether is recovered as a heads stream from the column; and
  (ii) methyl acetate is recovered as a base stream from the column; and which base stream or a part thereof is utilised as a methyl acetate feed to the co-production process.

Thus, advantageously, the present invention allows for a convenient means of recovering valuable dimethyl ether which, if desired, may be re-used as a feedstock, for example in carbonylation processes for the production of methyl acetate or in other chemical processes.

In one or more embodiments of the present invention, the co-production process forms parts of an integrated process which integrated process comprises a process for carbonylating dimethyl ether with a carbon monoxide-containing gas in the presence of a zeolite carbonylation catalyst wherein the degree of conversion of dimethyl ether is 1 to 95%, such as 5 to 90%, for example 5 to 60% per pass based on the total feed to carbonylation to produce a crude carbonylation product comprising methyl acetate and dimethyl ether, such as dimethyl ether in an amount 5 to 50 mol %; recovering from the crude carbonylation product a crude methyl acetate stream comprising methyl acetate and dimethyl ether; treating the crude methyl acetate stream or part thereof, suitably by distillation, to recover a stream comprising mainly dimethyl ether and a stream comprising methyl acetate and a reduced amount of dimethyl ether and wherein the stream, or a part thereof, comprising methyl acetate and a reduced amount of dimethyl ether, suitably dimethyl ether in an amount of greater than 0 to 25 mol %, based on the total feed to the process, is utilised as a feed to the co-production process. Preferably, in these embodiments, the stream comprising methyl acetate and a reduced amount of dimethyl ether comprises dimethyl ether in an amount, such as greater than 0 to 15 mol %, for instance greater than 0 to 10 mol %, preferably greater than 0 to 5 mol % based on the total feed to the process. In these embodiments, the crude methyl acetate stream may further comprise contaminants, such as one or both of acetone and acetaldehyde, in a total amount of >0 to 1 mol %, such as >0 to 0.25 mol %. There may be recovered from distillation, a stream comprising the majority of acetaldehyde present in a crude methyl acetate stream to be distilled, which stream may be and is preferably recovered from distillation as a separate stream, such as a sidedraw stream. Suitably, in these embodiments, a methanol stream comprising methanol and dimethyl ether is distilled together with the crude methyl acetate product stream to recover, suitably as a base stream from distillation, a stream comprising methyl acetate, methanol and dimethyl ether which recovered stream is utilised as a mixed feed for the co-production process. In these embodiments, the methanol stream comprising methanol and dimethyl ether further comprises methyl formate as a contaminant, for example in an amount of >0 to 1000 ppm and a stream comprising the majority of the methyl formate is recovered from the distillation, suitably recovered as a sidedraw stream. In these embodiments, the feed to the co-production process further comprises one or more of acetic acid, water and contaminants, such as one or more of acetaldehyde, acetone and methyl formate, in a total amount of 0 to 1 mol %, for example 0 to 0.25 mol %. Suitably, in these embodiments, the recovered stream from distillation, or part thereof, comprising mainly dimethyl ether, is returned to carbonylation for use therein as a feed.

As mentioned above, processes for the preparation of methyl acetate by carbonylating dimethyl ether feedstock with carbon monoxide in the presence of a catalyst are known, for example from U.S. Pat. No. 7,465,822, WO 2008/132438 and WO 2008/132441.

Processes for the carbonylation of dimethyl ether with carbon monoxide to produce crude methyl acetate may be carried out as heterogeneous vapour phase processes, typically employing reaction conditions of a temperature of about 100° C. to 350° C., for example of about 250° C. to 350° C. and a total pressure of about 1 to 200 barg (100 kPa to 20,000 kPa), for example about 50 to 100 barg (5000 kPa to 10,000 kPa).

Typically, the carbonylation process is carried out in the presence of a suitable carbonylation catalyst, for example a zeolite carbonylation catalyst. Suitable zeolite catalysts include aluminosilicate zeolites which comprise at least one channel which is defined by an 8-member ring. Preferably, the channel defined by the 8-member ring is interconnected with at least one channel defined by a ring with 10 or 12 members. Non-limiting examples of suitable aluminosilicate zeolites for use in the carbonylation process include zeolites of framework type MOR (for example, mordenite), FER (for example, ferrierite), OFF (for example, offretite) and GME (for example, gmelinite).

A zeolite may be utilised in a carbonylation process in an exchanged form with cations of one or more metals such as one or more of copper, silver, nickel, cobalt, iridium, palladium, rhodium and platinum. Mordenite zeolites containing copper and/or silver and loaded with 0.05 to 10 mol % platinum relative to aluminium are described in European patent application, EP-A-1985362. Alternatively, it may be used in substantially hydrogen form.

As-synthesised zeolites are typically in powder form, thus to provide mechanical strength to a zeolite catalyst may be utilised in the carbonylation process as a composite with any suitable binder material. Binder materials are selected such that the zeolite is suitably active and robust under the carbonylation process conditions. Examples of suitable binder materials include inorganic oxides, such as silicas, aluminas, alumina-silicates, magnesium silicates, magnesium aluminium silicates, titanias and zirconias. Preferred binder materials include aluminas, alumina-silicates and silicas.

To maintain the activity of the zeolite catalyst, the carbonylation process is preferably carried out under very low water conditions. Thus, it is preferred that feeds to the process such as dimethyl ether and carbon monoxide are dried prior to use in the process to reduce the total water fed to the process to an amount of 0.5 mol % or less.

Suitably, a carbonylation process may be carried out utilising a molar ratio of carbon monoxide to dimethyl ether in the range 1:1 to 99:1, for example 2:1 to 25:1.

Carbon monoxide is suitably utilised in the carbonylation process at a partial pressure in the range 0.1 to 100 barg (10 kPa to 10,000 kPa), for example about 10 to 65 barg (1000 kPa to 6500 kPa).

Carbon monoxide used as feedstock in such carbonylation processes may be employed as a gaseous mixture with hydrogen, such as a synthesis gas. The gaseous mixture/synthesis gas may also contain some carbon dioxide. The partial pressure of hydrogen may suitably be about 1 barg to 100 barg (100 kPa to 10,000 kPa), preferably about 10 to 75 barg (1000 kPa to 7500 kPa).

The carbonylation reaction may be carried out at a carbon monoxide:hydrogen molar ratio in the range 10:1 to 1:10, suitably at a molar ratio in the range 1:1 to 1:4 or higher.

Suitably, the total gas hourly space velocity of flow of gas through a catalyst bed (GHSV) is from about 500 to about 40,000 $h^{-1}$, for example from about 2000 to about 20,000 $h^{-1}$.

The conversion of dimethyl ether to methyl acetate product in a carbonylation process may be in the range 1 to 90% of the total carbonylation feed per pass, such as in the range 5 to 60%, for example in the range 30 to 60%. Operating the carbonylation process under conditions of a total pressure of about 50 to about 100 barg (5000 kPa to 10,000 kPa) and temperatures of about 250° C. to about 350° C. at low carbon monoxide partial pressure tends to decrease the conversion of dimethyl ether to methyl acetate.

In respect of carbonylation reactions carried out at dimethyl ether conversions of less than 100%, the crude carbonylation reaction product will comprise methyl acetate and unreacted dimethyl ether and may also contain carbon monoxide and, if present in feeds to carbonylation, one or more of hydrogen and carbon dioxide.

Crude methyl acetate may be recovered from the crude carbonylation reaction product by cooling the reaction product withdrawn, typically in vapour form, from a carbonylation reaction zone, to a temperature, for example in the range of 50° C. or less, in one or more conventional heat exchangers, and the cooled reaction product separated, for example in a knock-out drum or a tangential inlet drum, to recover a liquid crude methyl acetate comprising methyl acetate and dimethyl ether and a gaseous stream comprising the majority of the unconverted carbon monoxide and, if utilised in the carbonylation process, hydrogen and carbon dioxide.

Crude methyl acetate recovered from the crude carbonylation reaction product comprises mainly methyl acetate but also comprises dimethyl ether and may also comprise additional components selected from one or more of dissolved carbon oxides, hydrogen, methanol, water and acetic acid. As a result of side-reactions taking place in the carbonylation reaction the crude methyl acetate may also contain low levels of undesirable contaminants, for example one or both of acetaldehyde and acetone, such as in amounts of >0 to 1 mol %.

The amount of dimethyl ether present in crude methyl acetate recovered from carbonylation may vary and will depend on the degree of conversion of dimethyl ether reactant. Typically, for dimethyl ether conversions of less than 90% of total carbonylation feed per pass, for example for conversions in the range 5 to 60%, the crude methyl acetate may comprise dimethyl ether in an amount of from about 5 to 50 mol %.

The crude methyl acetate may further comprise small amounts of acetic acid and dissolved gases such as one or more of carbon oxides and hydrogen. Typically, a crude methyl acetate might comprise about 5 to 50 mol %, for example 5 to 25 mol % dimethyl ether, 1 to 5 mol % acetic acid, 0.5 to 3 mol % methanol and 1 to 4 mol % of carbon oxides and/or hydrogen and up to 1 mol % contaminants such as one or both of acetaldehyde and acetone, balance methyl acetate, for example 50 to 95 mol % methyl acetate.

Suitably, crude methyl acetate comprising methyl acetate and dimethyl ether, such as in an amount up to 50 mol % dimethyl ether, for example 5 to 25 mol % dimethyl ether, is treated to remove dimethyl ether therefrom by a distillation method.

In preferred embodiments, a crude methyl acetate comprising methyl acetate and dimethyl ether is treated to reduce its dimethyl ether content by distillation, preferably by fractional distillation. Preferably, in these embodiments distillation of the crude methyl acetate is carried out by fractional distillation in a distillation column wherein
  (i) dimethyl ether is recovered as a heads stream from the column; and
  (ii) methyl acetate is recovered as a base stream from the column; and which base stream or a part thereof is utilised as a methyl acetate feed to the co-production process Preference is given to a distillation method in which one or more distillation columns, preferably a single distillation column, is employed. In a typical configuration the distillation column has at least 5, such as at least 15 theoretical stages, such as at least 20 theoretical stages. Since distillation zones may have differing efficiencies 15 theoretical stages may be equivalent to at least 25 actual stages with an efficiency of about 0.7 or at least 30 actual stages with an efficiency of about 0.5.

Suitable distillation columns include tray or packed columns.

Suitably, a distillation column is operated at elevated pressure, such as at a pressure of about 0.5 barg (50 kPa) or more, such as about 0.5 barg to 30 barg (50 to 3000 kPa), for example about 10 to 30 barg (1000 to 3000 kPa).

In some or all embodiments, a distillation column has approximately 20 theoretical stages and is operated at a pressure of about 0.5 barg (50 kPa) or more, such as about 0.5 barg to 30 barg (50 to 3000 kPa), for example about 10 to 30 barg (100 to 2000 kPa) and suitably at a heads temperature of about 40 to 95° C.

Crude methyl acetate comprising dimethyl ether may be fed to the distillation column as a vapour and/or as a liquid. A heads stream comprising mainly dimethyl ether may be withdrawn from the column as a vapour and/or as a liquid. Typically, a heads stream might comprise at least 60 mol % dimethyl ether, for example 60 to 95 mol % dimethyl ether. At least a portion of a heads vapour stream may be condensed and a portion of the condensed liquid returned to the column as reflux.

The distillation column may be operated with a return of liquid reflux to the head of the column at a reflux to heads ratio dependent upon such factors as the desired heads stream composition. At operating pressures of from 10 to 30 barg (1000 to 3000 kPa) and a heads temperature of 40 to 90° C., a suitable reflux ratio is in the range 1 to 10, such as 1 to 4, for example 1.5 to 2.5. A suitable boil-up ratio may be 0.01 to 5.

The crude methyl acetate, for example crude methyl acetate derived from carbonylating dimethyl ether with carbon monoxide in the presence of a zeolite carbonylation catalyst and optionally hydrogen, may contain contaminants, such as one or both of acetaldehyde and acetone, for example in a total amount of 1 mol % or less. These contaminants can have a deleterious effect on certain catalysts and, in particular on solid Brønsted acid catalysts, such as heteropolyacid and zeolite catalysts, which may be employed as catalysts in processes for the co-production of acetic acid and dimethyl ether. Advantageously, the present invention further provides for some of these contaminants to be removed in addition to the removal of dimethyl ether from crude methyl acetate streams containing dimethyl ether and said contaminants, thereby reducing capital and production costs and alleviating complexity associated with the co-production process.

Contaminants, for example acetaldehyde, may be conveniently recovered from the distillation column as components of a stream which is withdrawn from the distillation column as a sidedraw stream. In such cases it is desirable that the sidedraw stream is withdrawn from the distillation column at a point above the feed point of the crude methyl acetate feed to the column. Recovery of contaminants in the sidedraw stream can be enhanced by providing sufficient stripping capacity in the distillation column below the feed point of the crude methyl acetate to the column. Thus, it is preferred that the distillation column has at least 3 theoretical stages, for example 3 to 10 theoretical stages, below the feed point of the crude methyl acetate feed to the column.

To optimise recovery of contaminants in the sidedraw stream, it is preferred that the sidedraw stream is withdrawn from the column at or near the point of maximum concentration of contaminants within the column. As would be recognised by the skilled person in the art, the point in the column at which the concentration of contaminants will be at its highest is dependent upon the specific operating conditions employed and, in particular the specific pressure, temperature and reflux ratio employed. Concentrations of components within the column can be readily determined, for example by compositional analysis of distillation mixtures at varying stages of the column, such as compositional analysis by gas chromatographic techniques.

Thus, typically, for a 40 stage column, the feed point of the crude methyl acetate to the column may be at stages 10 to 25 counted from the head of the column and a sidedraw stream may be withdrawn at stages 4 to 15 counted from the head, provided that the sidedraw is withdrawn from the column at a stage above the feed stage of the column.

In one or more embodiments of the present invention, the distillation column is a 40 stage column operated at a pressure of 10 to 30 barg, a heads temperature of 40 to 90° C. and a reflux ratio of from 1 to 4, the feed point of the crude methyl acetate feed to the column may be at stages 10 to 25 counted from the head of the column and the sidedraw stream withdrawn at stages 4 to 15 counted from the head.

Preferably, a sidedraw stream is withdrawn from the column as a liquid. In addition to contaminants, the sidedraw stream may further comprise amounts of one or both of dimethyl ether and methyl acetate.

A stream comprising principally methyl acetate is removed from the distillation column as a base stream from the column. The methyl acetate may be withdrawn from the distillation column as a liquid or as a vapour, preferably as a liquid.

Distillation of crude methyl acetate comprising methyl acetate and dimethyl ether, for example in amounts up to 50 mol %, is effective to recover from the distillation column methyl acetate having a dimethyl ether content of 25 mol % or less, such as 15 mol % or less, for example 10 mol % or less, preferably 5 mol % or less.

Distillation of crude methyl acetate comprising dimethyl ether, for example in amounts up to 50 mol %, and contaminants, for example acetaldehyde and acetone, up to a total amount of 1 mol % is effective to recover from the distillation column methyl acetate having a dimethyl ether content of 25 mol % or less, such as 15 mol % or less, for example 10 mol % or less, preferably 5 mol % or less and a total contaminant, for example acetaldehyde and acetone, content of less than 1 mol %, or 0.25 mol % or less, such as 200 ppm or less, for example 100 ppm or less or 50 ppm or less.

The methyl acetate stream, or a part thereof, recovered from distillation and comprising dimethyl ether in an amount of 25 mol % or less may be directly utilised in a process for the co-production of acetic acid and dimethyl ether without the need for further purification.

The dimethyl ether stream, or a part thereof, recovered from distillation of the crude methyl acetate stream may be utilised as a feed in processes in which the dimethyl ether is required as a starting material, such as a feed to a carbonylation process in which dimethyl ether is carbonylated with carbon monoxide in the presence of a carbonylation catalyst, for example a zeolite carbonylation catalyst, and optionally hydrogen, to produce methyl acetate or in another function. It is of course feasible to divide the recovered dimethyl ether stream into two or more streams and feed each stream to a different process.

The co-production process of the present invention to generate acetic acid and dimethyl ether requires methanol as a feedstock. In general, commercial sources of methanol contain low levels of methyl formate produced as a by-product of the methanol synthesis process. However, methyl formate in the presence of water readily hydrolyses to generate formic acid which is an undesirable contaminant in acetic acid products. Owing to the closeness of their boiling points, formic acid (bp 100.8° C.) and acetic acid (bp 118° C.) are difficult to separate from mixtures thereof by conventional fractional distillation techniques. Instead more complex extractive distillation methods are employed to achieve the required acetic acid product purities. Complex methods of this type for the separation of formic acid from acetic acid are described in, for example U.S. Pat. Nos. 4,692,219 and 5,227,029.

Conveniently, a crude methyl acetate stream comprising methyl acetate and dimethyl ether may be distilled together with a methanol stream comprising methanol and methyl formate as a contaminant and optionally comprising one or more both dimethyl ether and water so as to remove dimethyl ether and methyl formate therefrom to provide a purified methyl acetate and methanol feed mixture comprising >0 to 25 mol % dimethyl ether for use in the co-production process.

More advantageously, the present invention allows the methyl formate content of a methanol stream containing methyl formate to be reduced prior to its use in the co-production process, thereby avoiding the need for expensive and complex equipment to purify a co-production reaction product stream to separate acetic and formic acids therefrom.

A methanol feed to the distillation column may have a methyl formate content of up to about 1000 ppm mol.

Typically, commercially produced methanol also contains some dimethyl ether and may contain, for example up to 60 mol % dimethyl ether.

In some or all embodiments of the present invention, a methanol feed containing methyl formate, for example in amounts of 1000 ppm mol or less, is introduced into a distillation column, methanol is removed together with methyl acetate as a component of the base stream from the column and methyl formate is removed as a component of a sidedraw stream from the column.

Distillation of a mixture of crude methyl acetate, methanol and dimethyl ether in a total amount of, for example up to 60 mol % dimethyl ether, is effective to recover from distillation a stream comprising methyl acetate, methanol and dimethyl ether in an amount of 25 mol % or less, such as 15 mol % or less, for example 10 mol % or less, preferably 5 mol % or less.

In respect of mixtures of i) crude methyl acetate containing contaminants, such as acetaldehyde and acetone, in an amount up to 1 mol % and ii) methanol comprising methyl formate in an amount of, for example up to 1000 ppm mol, optionally dimethyl ether, such as up to 60 mol % dimethyl ether, distillation is effective to recover from a distillation column, a base stream comprising methyl acetate, methanol and contaminants, for example one or more of acetaldehyde, acetone and methyl formate, in a total amount of less than 1 mol %, such as 0.25 mol % or less, or 200 ppm or less, preferably 100 ppm or less, more preferably 50 ppm or less. The mixture to be distilled may further comprise water. Water may be removed from distillation as a component of the base stream.

In general, the feed to the co-production process may comprise methyl acetate in an amount of from 10 to 95 mol %, dimethyl ether in an amount of from 0.1 to 25 mol %, preferably 0.1 to 5 mol %, methanol in an amount of 0 to 50 mol %, preferably 5 to 20 mol %, and contaminants, such as one or more of acetaldehyde, acetone and methyl formate in a total amount of 0 to >1 mol %, for example 0 to 200 ppm. The feed to the co-production process may further comprise water.

In the co-production process of the present invention, a feed comprising methanol, methyl acetate and dimethyl ether in an amount of 25 mol % or less based on the total feed to the process is contacted in the presence of at least one catalyst to generate a reaction product comprising acetic acid and dimethyl ether. The hydrolysis of methyl acetate to produce acetic acid and dehydration of methanol to produce dimethyl ether can be represented by equations (1) and (2):

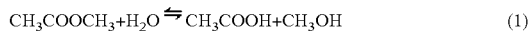  (1)

  (2)

In addition to any methyl acetate provided, for example as a stream from distillation, it is entirely feasible to supply one or more additional methyl acetate feeds to the co-production process provided that the total amount of dimethyl ether supplied to the co-production process is 25 mol % or less.

In a preferred embodiment of the present invention, methyl acetate for the co-production process is provided (excluding any methyl acetate recycle streams to the process) solely by a crude methyl acetate stream recovered from a process for the carbonylation of dimethyl ether and treated to reduce its dimethyl ether content so as to provide a methyl acetate feed to the co-production process which contains dimethyl ether and in an amount of 25 mol % or less.

Methanol feedstock for use in the co-production process may be imported methanol, for example from commercial methanol plants or that stored in storage tanks. Alternatively and/or additionally, methanol for use in the present invention may be that produced in-situ, for example as part of an integrated process with one or more of processes for the carbonylation of dimethyl ether to produce methyl acetate and co-production processes for the production of acetic acid and dimethyl ether from methyl acetate and methanol.

Methyl acetate and methanol may be supplied as separate feeds to the co-production process.

In a preferred embodiment, methanol is supplied to the co-production process as a mixture with methyl acetate, for example as a mixture recovered from distillation of a crude methyl acetate stream together with a methanol stream comprising methanol; the base stream from the distillation comprising methanol, methyl acetate and a reduced amount of dimethyl ether.

One or more catalysts may be utilised in the co-production process to catalyse the dehydration-hydrolysis reaction. Any suitable catalyst or catalysts may be used provided that it/they are effective to catalyse the hydrolysis of methyl acetate to produce acetic acid and are also effective to catalyse the dehydration of methanol to form dimethyl ether. One or more catalysts may be employed which are effective to catalyse both the hydrolysis and dehydration reactions. Alternatively, one or more catalysts effective for catalysing the hydrolysis may be used in addition to or as an admixture with one or more catalysts for the dehydration reaction. Where it is desired to employ two or more different catalysts, such catalysts may be utilised in the form of alternating catalyst beds or as one or more intimately mixed catalyst beds.

Preferably, one or more solid acid catalysts are utilised to catalyse the dehydration-hydrolysis reaction, such as one or more solid Brønsted acid catalysts. By 'Brønsted acid catalyst' is meant an acid catalyst which has the ability to donate an acidic proton to facilitate a chemical reaction. Solid acid catalysts useful for the dehydration of methanol include aluminas such as gamma-alumina and fluorinated alumina, acidic zirconias, aluminium phosphate, silica-alumina supported tungsten oxides and solid Brønsted acid catalysts such as heteropolyacids and salts thereof and aluminosilicate zeolites.

The term "heteropolyacid" as used herein and throughout this specification is meant to include the free acids. Heteropolyacids for use herein may be used either as free acids or as partial salts. Typically, the heteropolyacid, or the anionic component of its corresponding salt comprises 2 to 18 oxygen-linked polyvalent metal atoms, which are called peripheral atoms. These peripheral atoms surround one or more central atoms in a symmetrical manner. The peripheral atoms are usually one or more of molybdenum, tungsten, vanadium, niobium, tantalum and other metals. The central atoms are usually silicon or phosphorus but can comprise any one of a large variety of atoms from Groups I-VIII in the Periodic Table of elements. These include, for example cupric ions; divalent beryllium, zinc, cobalt or nickel ions; trivalent boron, aluminium, gallium, iron, cerium, arsenic, antimony, phosphorus, bismuth, chromium or rhodium ions; tetravalent silicon, germanium, tin, titanium, zirconium, vanadium, sulphur, tellurium, manganese nickel, platinum, thorium, hafnium, cerium ions and other rare earth ions; pentavalent phosphorus, arsenic, vanadium, antimony ions; hexavalent tellurium ions; and heptavalent iodine ions. Such heteropolyacids are also known as "polyoxoanions", "polyoxometallates" or "metal oxide clusters". The structures of some of the well-known anions are named after the original researchers in this field and are known, for example as Keggin, Wells-Dawson and Anderson-Evans-Perloff structures.

Heteropolyacids usually have a high molecular weight, for example in the range from 700-8500 and include dimeric complexes. They have a relatively high solubility in polar solvents such as water or other oxygenated solvents, especially if they are free acids and in the case of several salts, and their solubility can be controlled by choosing the appropriate counter-ions. Specific examples of heteropolyacids that may be usefully utilised in the present invention include the free acids such as silicotungstic acids, phosphotungstic acids and 12-tungstophosphoric acid ($H_3[PW_{12}O_{40}].xH_2O$); 12-molybdophosphoric acid ($H_3[PMo_{12}O_{40}].xH_2O$); 12-tungstosilicic acid ($H_4[SiW_{12}O_{40}].xH_2O$); 12-molybdosilicic acid ($H_4[SiMo_{12}O_{40}].xH_2O0$ and ammonium salts of heteropolyacids, such as ammonium salts of a phosphotungstic acid or a silicotungstic acid.

Zeolites known to be effective for the hydrolysis of methyl acetate to produce acetic acid include zeolite Y, zeolite A, zeolite X and mordenite. If desired, these zeolites can be usefully employed as a catalyst in the dehydration-hydrolysis reaction of the present invention.

Particularly useful zeolite catalysts for use in the co-production process to catalyse the dehydration-hydrolysis reaction include zeolites having a 2-dimensional or 3 dimensional channel system and at least one channel of which has a 10-membered ring. Specific non-limiting examples of such zeolites include zeolites of framework type FER (typified by ferrierite and ZSM-35), MFI (typified by ZSM-5), MFS (typified by ZSM-57), HEU (for example clinoptilolite) and NES (typified by NU-87).

The three-letter codes such as 'FER' refer to the framework structure type of the zeolites using the nomenclature proposed by the International Zeolite Association. Information about structure codes and zeolites is available in the Atlas of Zeolite Framework Types, C. H. Baerlocher, L. B. Mccusker and D. H. Olson, 6th Revised Edition, Elsevier, Amsterdam, 2007 and is also available on the website of the International Zeolite Association at www.iza-online.org.

The zeolite catalysts may be employed in an exchanged form. Exchanged forms of zeolites can be prepared by techniques such as ion-exchange and impregnation. These techniques are well-known in the art and typically involve the exchange of the hydrogen or ammonium cations of a zeolite with metal cations. For example, in the present invention, the zeolite may be in an exchanged form with one or more alkali metal cations for example sodium, lithium, potassium and cesium. Suitable exchanged form zeolites include ferrierite and ZSM-35 exchanged with one or more of sodium, lithium, potassium and cesium.

A zeolite may be used in the form of a composite with any suitable binder material. Examples of suitable binder materials include inorganic oxides, such as silicas, aluminas, alumina-silicates, magnesium silicates, magnesium aluminium silicates, titanias and zirconias. Preferred binder materials include aluminas, alumina-silicates and silicas. Suitably, a binder material may be present in the composite in an amount of from 10 to 90 wt % based on the total weight of zeolite and binder material.

The molar ratio of methanol to methyl acetate for use in the co-production process may be any desired ratio, but suitably the molar ratio of methanol:methyl acetate is in the range 1:0.1 to 1:20, for example 1:0.2 to 1:10.

The conversion of methyl acetate by hydrolysis to generate acetic acid requires a source of water. Water may be generated in-situ from dehydration of methanol feedstock. However, if desired, additional water may be supplied to the process, for example as a component of a methanol feed, methyl acetate feed or a mixed methanol and methyl acetate feed. Suitably, water is fed to the process in an amount of about 0.1 to 50 mol %, such as about 5 to 30 mol %, for example about 20 to 30 mol %, based on the total methyl acetate, water and methanol feed to the process.

The co-production process may be carried out as a heterogeneous vapour phase process or as a liquid phase process. If it is desired to conduct the process as a vapour phase process, it is preferable to volatilise liquid feed(s), for example in a pre-heater prior to contact with the catalyst.

The co-production process may be carried out at a temperature in the range 100 to 350° C. and at a pressure selected from atmospheric and pressures greater than atmospheric.

In one or more embodiments, the co-production process is conducted as a vapour phase process at a temperature of about 150° C. to 350° C. and a pressure of atmospheric to 30 barg (atmospheric to 3000 kPa), for example 5 to 20 barg (500 kPa to 2000 kPa). Suitably, in such cases, the dehydration-hydrolysis reaction is carried out at a gas hourly space velocity (GHSV) in the range 500 to 40,000 $h^{-1}$.

In one or more embodiments of the present invention, the co-production process is conducted as a liquid phase process carried out at a temperature of from about 140° C. to about 210° C. and at a pressure which is sufficient to maintain dimethyl ether product in solution, such as pressures of 40 barg (4000 kPa) or higher, for example 40 to 100 barg (4000 to 10,000 kPa). Suitably, in such cases, the co-production process is carried out at a liquid hourly space velocity (LHSV) in the range 0.2 to 20 $h^{-1}$.

The co-production process may be carried out using any suitable technique and apparatus, for example by reactive distillation. Reactive distillation techniques and apparatus therefor are well-known. A feed mixture comprising methanol and methyl acetate may be supplied to a conventional reactive distillation column, operated at, for example a pressure in the range atmospheric to 20 barg (atmospheric to 2000 kPa) and at a reaction temperature of about 100° C. to 250° C., to produce a crude reaction product comprising a mixture of acetic acid and dimethyl ether, which mixture is inherently separated within the reactive distillation column to recover a product stream rich in imethyl ether, typically recovered as a heads stream from the column, and a product stream rich in acetic acid which is typically recovered as a base stream from the column.

Alternatively, the co-production process may be carried out in a fixed bed reactor or a slurry bed reactor. Dimethyl ether has a low boiling point (−24° C.) and acetic acid has a high boiling point (118° C.). Thus, acetic acid and dimethyl ether may be recovered from the crude reaction product by conventional purification methods, such as by distillation in one or more conventional distillation columns. Suitable distillation columns include tray or packed columns. The temperatures and pressures employed in the columns can vary. Suitably, a distillation column may be operated at a pressure, for example of atmospheric to 20 barg (0 to 2000 kPa). Typically, a stream rich in dimethyl ether is recovered as a heads stream from the distillation column, and a stream rich in acetic acid is recovered as a base stream from the column.

In some or all embodiments of the present invention, the process further comprises recovering one or both of dimethyl ether and acetic acid from a crude reaction product comprising acetic acid and dimethyl ether.

The hydrolysis of methyl acetate and dehydration of methanol are equilibrium reactions, and thus typically the crude reaction product also comprises one or more of unreacted methanol and unreacted methyl acetate and it may also comprise water. Consequently, one or both of acetic acid and dimethyl ether streams recovered from the crude reaction product may also comprise one or more additional components selected from methanol, methyl acetate and water. Methanol, methyl acetate and water may be removed from recovered acetic acid and dimethyl ether streams, for example by conventional purification processes, such as by fractional distillation in one or more distillation columns.

Suitably one or more streams comprising components recovered from the crude reaction product comprising acetic acid and dimethyl ether (recycle streams), for example one or more of methanol, methyl acetate and water are returned to the co-production process.

Dimethyl ether recovered from the crude reaction product comprising acetic acid and dimethyl ether may be sold or used as a fuel or utilised as a feedstock in processes for the carbonylation of dimethyl ether to produce methyl acetate or in other chemical processes.

Acetic acid recovered from the crude reaction product may be sold or may be used as a feedstock in a variety of chemical processes, such as the manufacture of vinyl acetate or ethyl acetate.

The co-production process may be operated as a continuous process or as a batch process, preferably operated as a continuous process.

BRIEF DESCRIPTION OF THE DRAWINGS

The invention is further described with reference to the accompanying drawings, in which.

The invention is now illustrated with reference to the following non-limiting Examples.

EXAMPLE 1

Figure 1:
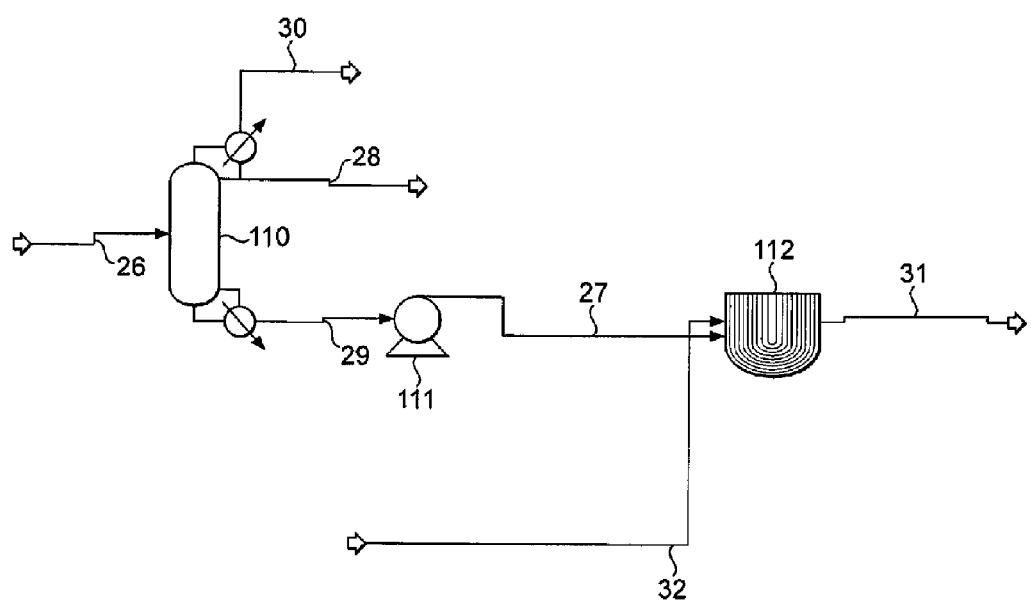
FIG. 1 illustrates schematically a distillation column (110) for carrying out embodiments of the process of the present invention.

This Example demonstrates a process for purifying a crude methyl acetate feed comprising dimethyl ether for utilisation in the co-production of acetic acid and dimethyl ether in accordance with the present invention. Reference is made to FIG. 1 and Table 1. FIG. 1 illustrates schematically a distillation column (110) for carrying out embodiments of the process of the present invention. A feed stream (26) comprising principally methyl acetate and having a dimethyl ether content of 17.8 mol % is introduced into distillation column (110). Distillation column (110) has 20 theoretical stages with the feed point on stage 10 (counted from the head of the column) and is operated at a pressure of 11.7 barg, a heads temperature of 45° C. and a base temperature of 154° C., a reflux ratio of 2.2 and a boil-up ratio of 0.69. A vent stream (30) comprising mainly carbon oxides and hydrogen is withdrawn from column (110). A heads stream (28) comprising mainly dimethyl ether is removed from the column (110). A stream (29) comprising mainly methyl acetate with 0.5 mol % dimethyl ether is removed as a base stream from the column (110) and pumped via high-pressure pump (111) as stream (27) to a dehydration-hydrolysis reaction unit (112) such as a fixed bed reactor containing a solid acid catalyst such as a zeolite catalyst and operated at elevated pressure and temperature of 100 to 350° C. and contacted therein with a methanol feed (32) to generate a crude reaction product comprising acetic acid and dimethyl ether.

Utilising the procedure and apparatus of the type illustrated in FIG. 1, simulations were carried out using ASPEN software version 7.3. The stream compositions (in kmol/hr and mol %) employed in this Example are shown in Table 1 below. In the Table, the following abbreviations are used:

CO—carbon monoxide
$CO_2$—carbon dioxide
$H_2$—hydrogen
MeOH—methanol
AcOH—acetic acid
$H_2O$—water
DME—dimethyl ether
MeOAc—methyl acetate

EXAMPLE 2

Figure 2:
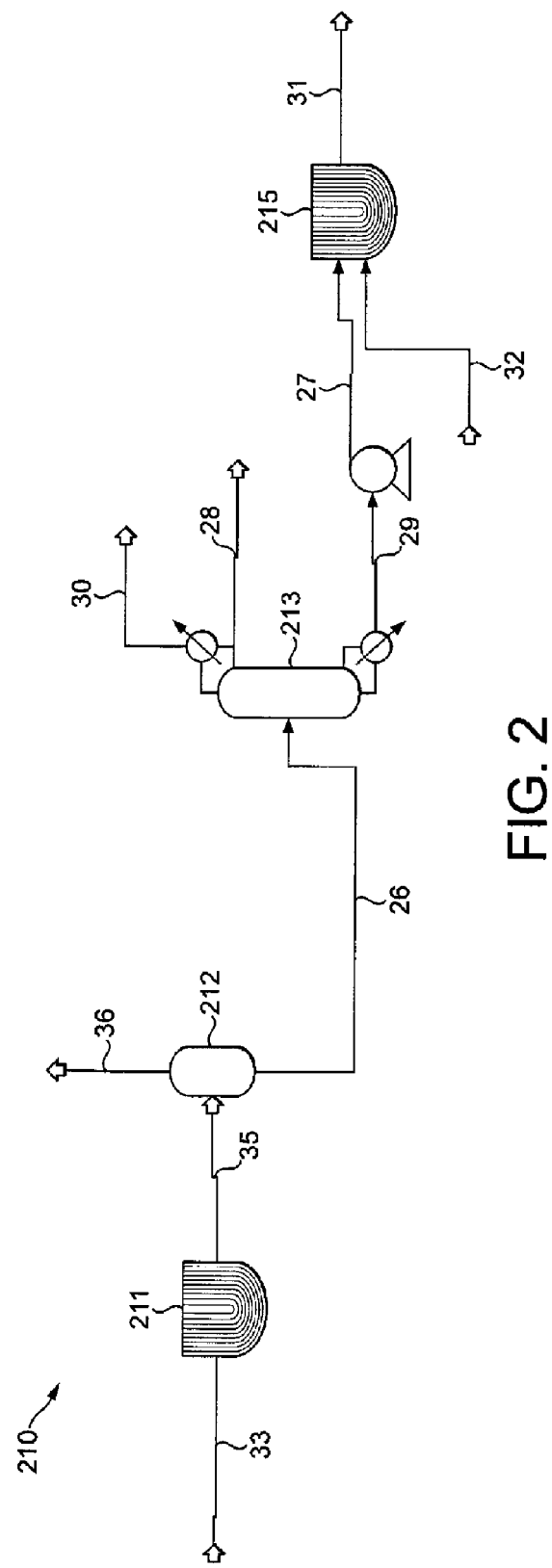
FIG. 2 illustrates schematically an integrated unit (210) for carrying out embodiments of the present invention.

This Example demonstrates a process for purifying a crude methyl acetate feed comprising dimethyl ether recovered from a process for the carbonylation of dimethyl ether with carbon monoxide in the presence of a catalyst and hydrogen for utilisation in the co-production of acetic acid and dimethyl ether in accordance with the present invention. Reference is made to FIG. 2 and Table 2.

FIG. 2 illustrates schematically an integrated unit (210) for carrying out embodiments of the present invention. A feed stream (33) comprising dimethyl ether, carbon monoxide and hydrogen is fed to a carbonylation reaction unit (211) such as a fixed bed reactor operated at a pressure of, for example 50 to 100 barg and at a temperature of, for example about 250 to 350° C. and is contacted therein with a zeolite carbonylation catalyst to produce a crude carbonylation reaction product withdrawn from the reaction unit (211) as stream (35). Stream (35) is passed to a gas-liquid separation unit (212) where it is separated into a gaseous stream (36) and a liquid stream (26) comprising mainly methyl acetate and having a dimethyl ether content of 25.2 mol %. The feed stream (26) is introduced into distillation column (213). Distillation column (213) has 20 theoretical stages with the feed point on stage 10 (counted from the head of the column) and is operated at a pressure of 11.7 barg, a heads temperature of 40° C. and a base temperature of 154° C., a reflux ratio of 0.58 and a boil-up ratio of 1.2. A vent stream (30) comprising mainly carbon oxides and hydrogen is withdrawn from column (213). A heads stream (28) comprising mainly dimethyl ether is removed from the column (213). A stream (29) comprising mainly methyl acetate with 0.5 mol % dimethyl ether is removed as a base stream from the column (213) and pumped via high-pressure pump (214) as stream (27) to a dehydration-hydrolysis reaction unit (215) such as a fixed bed reactor operated at elevated pressure and temperature of, for example 100 to 350° C. and together with a methanol feed (32) contacted therein with a solid acid catalyst such as a zeolite catalyst to generate a crude reaction product comprising acetic acid and dimethyl ether. Utilising the procedure and apparatus of the type illustrated in FIG. 2, simulations were carried out using ASPEN software version 7.3. The stream compositions (in kmol/hr and mol %) employed in this Example are shown in Table 2 below. The abbreviations used in Table 2 have the meanings as used in respect of Table 1 above with the addition of $CH_4$-methane.

TABLE 1

| | Stream mol flow/mol % | | | | | | | | | | | |
|---|---|---|---|---|---|---|---|---|---|---|---|---|
| | 26 | | 28 | | 29 | | 30 | | 31 | | 32 | |
| CO | 2.0 | 0.1 | 0.1 | 0.0 | 0.0 | 0.0 | 1.9 | 3.2 | 0.0 | 0.0 | 0.0 | 0.0 |
| $CO_2$ | 6.0 | 0.2 | 3.5 | 0.9 | 0.0 | 0.0 | 2.5 | 4.4 | 0.0 | 0.0 | 0.0 | 0.0 |
| $H_2$ | 7.0 | 0.3 | 0.4 | 0.1 | 0.0 | 0.0 | 6.6 | 11.5 | 0.0 | 0.0 | 0.0 | 0.0 |
| MeOH | 38.0 | 1.6 | 0.6 | 0.2 | 37.4 | 1.9 | 0.0 | 0.0 | 290.4 | 7.0 | 2040.0 | 92.6 |
| AcOH | 47.0 | 2.0 | 0.0 | 0.0 | 47.0 | 2.4 | 0.0 | 0.0 | 226.7 | 5.4 | 0.0 | 0.0 |
| $H_2O$ | 8.0 | 0.3 | 0.9 | 0.2 | 7.0 | 0.4 | 0.0 | 0.0 | 810.6 | 19.4 | 0.0 | 0.0 |
| DME | 429.0 | 17.8 | 372.9 | 98.0 | 9.8 | 0.5 | 46.3 | 80.7 | 1156.2 | 27.7 | 163.0 | 7.4 |
| MeOAc | 1868.0 | 77.7 | 2.1 | 0.5 | 1865.9 | 94.9 | 0.0 | 0.0 | 1686.2 | 40.4 | 0.0 | 0.0 |

TABLE 2

| | Stream mol flow/mol % | | | | | | | | | |
|---|---|---|---|---|---|---|---|---|---|---|
| | 33 | | 35 | | 36 | | 26 | | 28 | |
| CO | 7200.0 | 16.9 | 4850.0 | 12.1 | 4825.9 | 13.0 | 24.1 | 0.8 | 0.1 | 0.0 |
| CO$_2$ | 1600.0 | 3.8 | 1600.0 | 4.0 | 1479.9 | 4.0 | 120.1 | 4.0 | 8.1 | 3.4 |
| CH$_4$ | 0.0 | 0.0 | 94.0 | 0.2 | 92.9 | 0.2 | 1.1 | 0.0 | 0.0 | 0.0 |
| H$_2$ | 29000.0 | 68.2 | 28906.0 | 72.0 | 28835.6 | 77.6 | 70.4 | 2.4 | 0.2 | 0.1 |
| MeOH | 0.0 | 0.0 | 31.1 | 0.1 | 4.7 | 0.0 | 26.4 | 0.9 | 0.1 | 0.0 |
| AcOH | 0.0 | 0.0 | 31.1 | 0.1 | 0.4 | 0.0 | 30.6 | 1.0 | 0.0 | 0.0 |
| H$_2$O | 0.0 | 0.0 | 15.9 | 0.0 | 4.3 | 0.0 | 11.6 | 0.4 | 0.2 | 0.1 |
| DME | 4700.0 | 11.1 | 2303.0 | 5.7 | 1555.7 | 4.2 | 747.3 | 25.2 | 226.4 | 96.3 |
| MeOAc | 0.0 | 0.0 | 2318.9 | 5.8 | 382.8 | 1.0 | 1936.1 | 65.2 | 0.1 | 0.0 |

| | Stream mol flow/mol % | | | | | | | |
|---|---|---|---|---|---|---|---|---|
| | 29 | | 30 | | 31 | | 32 | |
| CO | 0.0 | 0.0 | 24.0 | 3.3 | 0.0 | 0.0 | 0.0 | 0.0 |
| CO2 | 0.0 | 0.0 | 112.0 | 15.6 | 0.0 | 0.0 | 0.0 | 0.0 |
| CH$_4$ | 0.0 | 0.0 | 1.1 | 0.2 | 0.0 | 0.0 | 0.0 | 0.0 |
| H2 | 0.0 | 0.0 | 70.2 | 9.8 | 0.0 | 0.0 | 0.0 | 0.0 |
| MeOH | 26.3 | 1.3 | 0.0 | 0.0 | 289.2 | 6.9 | 2040.0 | 92.6 |
| AcOH | 30.6 | 1.5 | 0.0 | 0.0 | 230.6 | 5.5 | 0.0 | 0.0 |
| H$_2$O | 11.3 | 0.6 | 0.1 | 0.0 | 799.9 | 19.0 | 0.0 | 0.0 |
| DME | 10.1 | 0.5 | 510.8 | 71.1 | 1161.6 | 27.5 | 163.0 | 7.4 |
| MeOAc | 1936.0 | 96.1 | 0.0 | 0.0 | 1736.1 | 41.2 | 0.0 | 0.0 |

EXAMPLE 3

Figure 3:
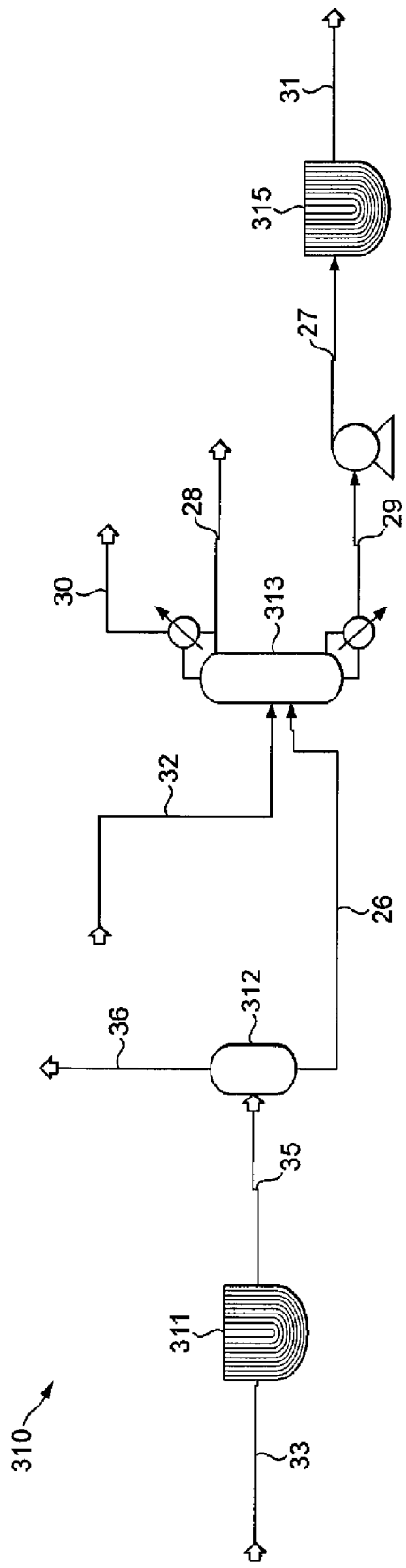
FIG. 3 illustrates schematically an integrated unit (310) for carrying out embodiments of the process of the present invention.

This Example demonstrates a process for purifying a crude methyl acetate feed comprising dimethyl ether recovered from a process for the carbonylation of dimethyl ether with carbon monoxide in the presence of a catalyst and hydrogen together with a methanol feed comprising dimethyl ether for utilisation in the co-production of acetic acid and dimethyl ether in accordance with the present invention. Reference is made to FIG. 3 and Table 3.

FIG. 3 illustrates schematically an integrated unit (310) for carrying out embodiments of the process of the present invention. A feed stream (33) comprising dimethyl ether, carbon monoxide and hydrogen is fed to a carbonylation reaction unit (311) such as a fixed bed reactor operated at a pressure of, for example 50 to 100 barg and at a temperature of, for example about 250 to 350° C. and is contacted therein with a zeolite carbonylation catalyst to produce a crude carbonylation reaction product withdrawn from the reaction unit (311) as stream (35). Stream (35) is passed to a gas-liquid separation unit (312) where it is separated into a gaseous stream (36) and a liquid stream (26) comprising mainly methyl acetate and having a dimethyl ether content of 25.2 mol %. Distillation column (313) has 20 theoretical stages with the feed point on stage 10 (counted from the head of the column) and is operated at a pressure of 11.7 barg, a heads temperature of 40° C. and a base temperature of 143° C., a reflux ratio of 2.6 and a boil-up ratio of 1.2. The feed stream (26) comprising mainly methyl acetate is introduced into distillation column (313) together with a feed stream (32) comprising mainly methanol and a small amount of dimethyl ether onto feed stage 10 of the distillation column (313). A vent stream (30) comprising mainly carbon oxides and hydrogen is withdrawn from column (313). A heads stream (28) comprising mainly dimethyl ether is removed from the column (313). A stream (29) comprising mainly methyl acetate and methanol and 0.5 mol % dimethyl ether is removed as a base stream from the column (313) and pumped via high-pressure pump (314) as stream (27) to a dehydration-hydrolysis reaction unit (315) such as a fixed bed reactor operated at elevated pressure and temperature of, for example 100 to 350° C. and contacted therein with a solid acid catalyst such as a zeolite catalyst to generate a crude reaction product comprising acetic acid and dimethyl ether.

Utilising the procedure and apparatus of the type illustrated in FIG. 3, simulations were carried out using ASPEN software version 7.3. The stream compositions (in kmol/hr and mol %) employed in this Example are shown in Table 3 below. The abbreviations used in Table 3 have the same meanings as in respect of Tables 1 and 2 above

TABLE 3

| | Stream mol flow/mol % | | | | | | | | | |
|---|---|---|---|---|---|---|---|---|---|---|
| | 33 | | 35 | | 36 | | 26 | | 28 | |
| CO | 7200.0 | 16.9 | 4850.0 | 12.1 | 4825.9 | 13.0 | 24.1 | 0.8 | 0.2 | 0.0 |
| CO$_2$ | 1600.0 | 3.8 | 1600.0 | 4.0 | 1479.9 | 4.0 | 120.1 | 4.0 | 13.6 | 3.4 |
| CH$_4$ | 0.0 | 0.0 | 94.0 | 0.2 | 92.9 | 0.2 | 1.1 | 0.0 | 0.0 | 0.0 |
| H$_2$ | 29000.0 | 68.2 | 28906.0 | 72.0 | 28835.6 | 77.6 | 70.4 | 2.4 | 0.3 | 0.1 |
| MeOH | 0.0 | 0.0 | 31.1 | 0.1 | 4.7 | 0.0 | 26.4 | 0.9 | 0.4 | 0.1 |
| AcOH | 0.0 | 0.0 | 31.1 | 0.1 | 0.4 | 0.0 | 30.6 | 1.0 | 0.0 | 0.0 |
| H$_2$O | 0.0 | 0.0 | 15.9 | 0.0 | 4.3 | 0.0 | 11.6 | 0.4 | 0.0 | 0.0 |
| DME | 4700.0 | 11.1 | 2303.0 | 5.7 | 1555.7 | 4.2 | 747.3 | 25.2 | 391.4 | 96.4 |
| MeOAc | 0.0 | 0.0 | 2318.9 | 5.8 | 382.8 | 1.0 | 1936.1 | 65.2 | 0.0 | 0.0 |

TABLE 3-continued

| | Stream mol flow/mol % | | | | | | | |
|---|---|---|---|---|---|---|---|---|
| | 29 | | 30 | | 31 | | 32 | |
| CO | 0.0 | 0.0 | 24.0 | 3.4 | 0.0 | 0.0 | 0.0 | 0.0 |
| CO$_2$ | 0.0 | 0.0 | 106.5 | 15.2 | 0.0 | 0.0 | 0.0 | 0.0 |
| CH$_4$ | 0.0 | 0.0 | 1.1 | 0.2 | 0.0 | 0.0 | 0.0 | 0.0 |
| H$_2$ | 0.0 | 0.0 | 70.1 | 10.0 | 0.0 | 0.0 | 0.0 | 0.0 |
| MeOH | 2065.8 | 50.8 | 0.2 | 0.0 | 271.9 | 6.7 | 2040.0 | 92.6 |
| AcOH | 30.6 | 0.8 | 0.0 | 0.0 | 245.9 | 6.1 | 0.0 | 0.0 |
| H$_2$O | 11.6 | 0.3 | 0.0 | 0.0 | 800.9 | 19.7 | 0.0 | 0.0 |
| DME | 20.3 | 0.5 | 498.5 | 71.2 | 1024.9 | 25.2 | 163.0 | 7.4 |
| MeOAc | 1936.1 | 47.6 | 0.0 | 0.0 | 1720.8 | 42.3 | 0.0 | 0.0 |

EXAMPLE 4

Figure 4:
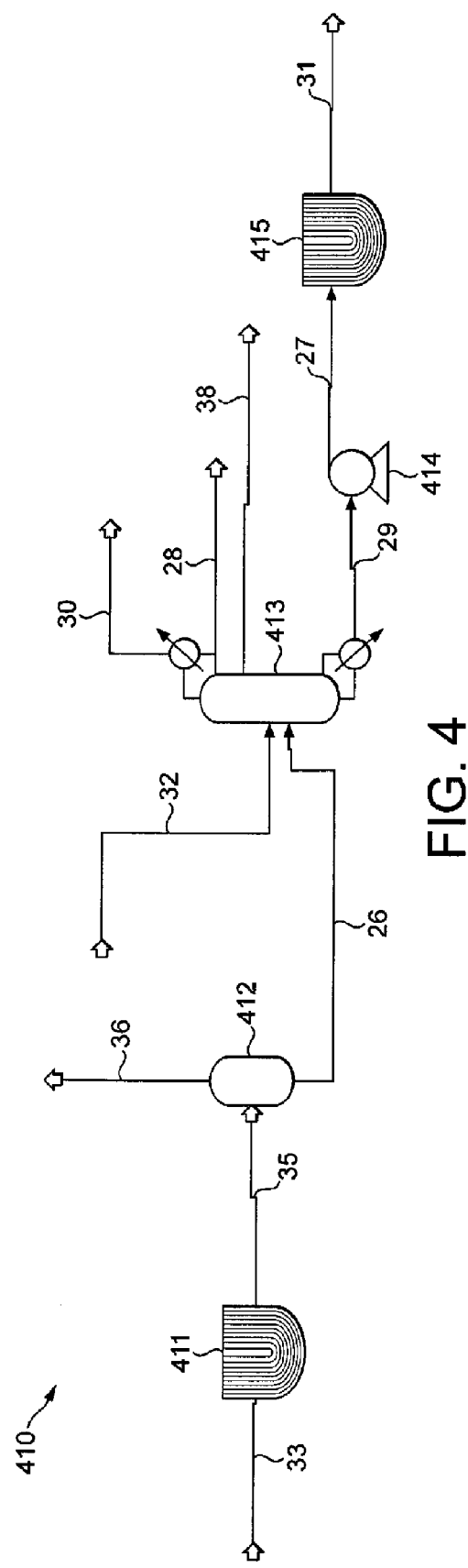
FIG. 4 illustrates schematically an integrated unit (410) for carrying out embodiments of the process of the present invention.

This Example demonstrates a process for purifying a crude methyl acetate feed comprising dimethyl ether and acetaldehyde/acetone contaminants recovered from a process for the carbonylation of dimethyl ether with carbon monoxide in the presence of a catalyst and hydrogen together with a methanol feed comprising dimethyl ether and methyl formate contaminant for utilisation in the co-production of acetic acid and dimethyl ether in accordance with the present invention. Reference is made to FIG. 4 and Table 4.

FIG. 4 illustrates schematically an integrated unit (410) for carrying out embodiments of the process of the present invention. A feed stream (33) comprising dimethyl ether, carbon monoxide and hydrogen is fed to a carbonylation reaction unit (411) such as a fixed bed reactor operated at a pressure of, for example 50 to 100 barg and at a temperature of for example about 250 to 350° C. and is contacted therein with a zeolite carbonylation catalyst to produce a crude carbonylation reaction product containing contaminants withdrawn from the reaction unit (411) as stream (35). Stream (35) is passed to a gas-liquid separation unit (412) where it is separated into a gaseous stream (36) and a liquid stream (26) comprising mainly methyl acetate, a dimethyl ether content of 25.4 mol % and a total of less than 1 mol % acetaldehyde and acetone. Distillation column (413) has 30 theoretical stages with feed points on stages 10 and 21 and sidedraw take-off at stage 6 (counted from the head of the column) and is operated at a pressure of 11.7 barg, a heads temperature of 40° C. and a base temperature of 144° C., a reflux ratio of 8.8 and a boil-up ratio of 2.4. The feed stream (26) comprising mainly methyl acetate is introduced into distillation column (413) onto feed stage 21 of the distillation column (313). A feed stream (32) comprising mainly methanol, a small amount of dimethyl ether and less than 0.1 mol % methyl formate is introduced into column (413) on stage 10. A vent stream (30) comprising mainly carbon oxides and hydrogen is withdrawn from column (413). A heads stream (28) comprising mainly dimethyl ether is removed from the column (413). The majority of the acetaldehyde/acetone/methyl formate contaminants are withdrawn from column (413) as components of sidedraw stream (38). A stream (29) comprising mainly methyl acetate and methanol, 0.1 mol % dimethyl ether and a reduced quantity of acetaldehyde/methyl formate/acetone contaminants is removed as a base stream from the column (413) and pumped via high-pressure pump (414) as stream (27) to a dehydration-hydrolysis reaction unit (415) such as a fixed bed reactor operated at elevated pressure and temperature of, for example 100 to 350° C. and contacted therein with a solid acid catalyst such as a zeolite catalyst to generate a crude reaction product comprising acetic acid and dimethyl ether.

Utilising the procedure and apparatus of the type illustrated in FIG. 4, simulations were carried out using ASPEN software version 7.3. The stream compositions (in kmol/hr and mol %) employed in this Example are shown in Table 4 below. The abbreviations used in Table 4 have the same meanings as those used in Tables 1 and 2 above with the addition of MeOFO—methyl formate; and AcH—acetaldehyde.

TABLE 4

| | Stream mol flow/mol % | | | | | | | | | |
|---|---|---|---|---|---|---|---|---|---|---|
| | 33 | | 35 | | 36 | | 26 | | 28 | |
| CO | 7200.0 | 16.9 | 4842.6 | 12.1 | 4818.3 | 13.0 | 24.3 | 0.8 | 0.2 | 0.0 |
| CO$_2$ | 1600.0 | 3.8 | 1607.4 | 4.0 | 1485.9 | 4.0 | 121.5 | 4.1 | 12.9 | 3.4 |
| CH$_4$ | 0.0 | 0.0 | 47.0 | 0.1 | 46.4 | 0.1 | 0.6 | 0.0 | 0.0 | 0.0 |
| H$_2$ | 29000.0 | 68.2 | 28939.4 | 72.1 | 28868.5 | 77.6 | 70.9 | 2.4 | 0.3 | 0.1 |
| MeOH | 0.0 | 0.0 | 29.4 | 0.1 | 5.2 | 0.0 | 24.2 | 0.8 | 0.4 | 0.1 |
| AcOH | 0.0 | 0.0 | 15.8 | 0.0 | 0.3 | 0.0 | 15.5 | 0.5 | 0.0 | 0.0 |
| H$_2$O | 0.0 | 0.0 | 7.7 | 0.0 | 2.5 | 0.0 | 5.2 | 0.2 | 0.0 | 0.0 |
| DME | 4700.0 | 11.1 | 2326.5 | 5.8 | 1572.9 | 4.2 | 753.6 | 25.4 | 366.6 | 96.3 |
| MeOAc | 0.0 | 0.0 | 2313.2 | 5.8 | 380.9 | 1.0 | 1932.3 | 65.2 | 0.001 | 0.0 |
| Acetone | 0.0 | 0.0 | 7.4 | 0.018 | 1.4 | 0.004 | 6.1 | 0.204 | 0.0 | 0.0 |
| MeOFO | 0.0 | 0.0 | 0.0 | 0.0 | 0.0 | 0.0 | 0.0 | 0.0 | 0.044 | 0.011 |
| AcH | 0.0 | 0.0 | 13.6 | 0.034 | 5.2 | 0.014 | 8.4 | 0.282 | 0.418 | 0.110 |

| | Stream mol flow/mol % | | | | | | | | | |
|---|---|---|---|---|---|---|---|---|---|---|
| | 29 | | 30 | | 31 | | 32 | | 38 | |
| CO | 0.0 | 0.0 | 24.1 | 3.4 | 0.0 | 0.0 | 0.0 | 0.0 | 0.0 | 0.0 |
| CO$_2$ | 0.0 | 0.0 | 108.4 | 15.4 | 0.0 | 0.0 | 0.0 | 0.0 | 0.1 | 0.1 |
| CH$_4$ | 0.0 | 0.0 | 0.5 | 0.1 | 0.0 | 0.0 | 0.0 | 0.0 | 0.0 | 0.0 |

TABLE 4-continued

| | | | | | | | | | | |
|---|---|---|---|---|---|---|---|---|---|---|
| H₂ | 0.0 | 0.0 | 70.6 | 10.0 | 0.0 | 0.0 | 0.0 | 0.0 | 0.0 | 0.0 |
| MeOH | 2028.0 | 50.9 | 0.2 | 0.0 | 263.7 | 6.6 | 2040.0 | 92.5 | 35.7 | 35.7 |
| AcOH | 15.5 | 0.4 | 0.0 | 0.0 | 241.5 | 6.1 | 0.0 | 0.0 | 0.0 | 0.0 |
| H₂O | 5.2 | 0.1 | 0.0 | 0.0 | 774.4 | 19.5 | 0.0 | 0.0 | 0.0 | 0.0 |
| DME | 2.0 | 0.1 | 501.5 | 71.1 | 997.1 | 25.0 | 163.0 | 7.4 | 46.6 | 46.6 |
| MeOAC | 1923.8 | 48.3 | 0.0 | 0.0 | 1697.9 | 42.6 | 0.0 | 0.0 | 8.5 | 8.5 |
| Acetone | 6.1 | 0.2 | 0.0 | 0.0 | 6.1 | 0.2 | 0.0 | 0.0 | 0.001 | 0.001 |
| MeOFO | 0.009 | 0.0002 | 0.014 | 0.002 | 0.006 | 0.0001 | 2.0 | 0.091 | 1.93 | 1.93 |
| AcH | 0.543 | 0.014 | 0.163 | 0.023 | 0.543 | 0.014 | 0.0 | 0.0 | 7.23 | 7.23 |

The invention claimed is:

1. A process for the co-production of acetic acid and dimethyl ether by dehydration-hydrolysis of a feed mixture of methanol and methyl acetate in the presence of at least one catalyst, which catalyst is a solid acid catalyst, to generate a crude reaction product comprising acetic acid and dimethyl ether, said process comprising feeding to said co-production process a feed comprising methanol, methyl acetate and dimethyl ether, wherein the dimethyl ether is present in the feed in a total amount of 25 mol % or less based on the total feed.

2. A process according to claim 1 wherein the feed to the co-production process comprises methyl acetate in an amount of from 10 to 95 mol %, dimethyl ether in an amount of from 0.1 to 25 mol %, methanol in an amount of 5 to 20 mol % and contaminants in a total amount of 0 to less than 1 mol %.

3. A process according to claim 2 wherein the contaminants are selected from one or more of acetaldehyde, acetone and methyl formate.

4. A process according to claim 2 wherein the feed comprises dimethyl ether in an amount of 0.1 to 5 mol %.

5. A process according to claim 2 wherein the feed further comprises water.

6. A process according to claim 1 wherein the methyl acetate feed comprises dimethyl ether and is derived from a crude methyl acetate stream produced in processes for carbonylation of dimethyl ether with carbon monoxide in the presence of a carbonylation catalyst to produce a crude methyl acetate stream comprising dimethyl ether which crude methyl acetate stream is treated to reduce its dimethyl ether content to provide a methyl acetate feed to the co-production process which comprises dimethyl ether in an amount of >0 to 25 mol %.

7. A process according to claim 6 wherein the treated crude methyl acetate comprises dimethyl ether in an amount of >0 to 5 mol %.

8. A process according to claim 6 wherein the crude methyl acetate comprises dimethyl ether in an amount of 5 to 50 mol %.

9. A process according to claim 8 wherein the crude methyl acetate further comprises contaminants in a total amount of up to 1 mol %.

10. A process according to claim 6 wherein the crude methyl acetate is treated to reduce its dimethyl ether content by distillation.

11. A process according to claim 10 wherein the distillation is carried out at a pressure of from 10 to 30 barg (1000 to 3000 kPa) and a heads temperature of 40 to 90 ° C.

12. A process according to claim 1 wherein the solid acid catalyst is a zeolite catalyst.

13. A process according to claim 1 wherein the co-production process is carried out at a temperature in the range 100 to 350 ° C. and at a pressure selected from atmospheric and pressures greater than atmospheric.

14. A process according to claim 1 which further comprises recovering dimethyl ether from the crude reaction product comprising acetic acid and dimethyl ether.

15. A process according to claim 14 wherein recovered dimethyl ether, or a part thereof, is utilised as a feed to a carbonylation process in which dimethyl ether is carbonylated with carbon monoxide in the presence of a carbonylation catalyst to produce a crude methyl acetate.

16. A process according to claim 1 wherein acetic acid is recovered from the crude reaction product comprising acetic acid and dimethyl ether.

17. A process according to claim 1 wherein the co-production process forms part of an integrated process which integrated process comprises carbonylating dimethyl ether with a carbon monoxide-containing gas in the presence of a zeolite carbonylation catalyst wherein conversion of dimethyl ether is 5 to 90 mol % per pass based on total feed to carbonylation to produce a crude carbonylation product comprising methyl acetate and dimethyl ether, recovering from the crude carbonylation product a crude methyl acetate stream comprising methyl acetate and dimethyl ether, treating the crude methyl acetate stream, or part thereof, to recover a stream comprising mainly dimethyl ether and a stream comprising methyl acetate and a reduced amount of dimethyl ether and wherein the stream, or a part thereof, comprising methyl acetate and a reduced amount of dimethyl ether which is an amount of >0 to 25 mol % based on total feed to the process, is utilised as a feed to the co-production process.

18. A process according to claim 1 wherein the co-production process is operated as a continuous process.

* * * * *